US00PP23788P3

(12) United States Plant Patent
Schoone

(10) Patent No.: US PP23,788 P3
(45) Date of Patent: Jul. 30, 2013

(54) ***PHALAENOPSIS* ORCHID PLANT NAMED 'LOOKING BACK'**

(50) Latin Name: *Phalaenopsis hybrida*
Varietal Denomination: Looking Back

(75) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days.

(21) Appl. No.: 13/067,308

(22) Filed: May 24, 2011

(65) Prior Publication Data

US 2012/0102607 P1 Apr. 26, 2012

(30) Foreign Application Priority Data

Oct. 20, 2010 (NL) ..... PBR OPS731

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP

(57) ABSTRACT

A new and distinct *Phalaenopsis* plant named 'Looking Back' particularly characterized by flowers which are white with purple marks; the labellum is yellow with some purple and white; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Looking Back'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Looking Back'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Looking Back' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Looking Back' originated from a cross made by the inventor in 1998 in Strengweg, Heemskerk, The Netherlands. The female or seed parent is the *Phalaenopsis* cultivar designated 'Free Spirit', unpatented. The male or pollen parent is the *Phalaenopsis* cultivar designated 'Tying Shin Cupid', unpatented. The new *Phalaenopsis* 'Looking Back' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture was first performed in January, 2006 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Looking Back', which in combination distinguish this *Phalaenopsis* as a new and distinct cultivar:

1. flowers which are white with purple marks; the labellum is yellow with some purple and white;
2. plant produces more than one inflorescence;

3. plants may be propagated economically and uniformly using tissue culture;
4. inflorescence is long and sturdy
5. relatively short, dark-green foliage Presently, there is no other commercial cultivar to which 'Looking Back' can be meaningfully compared.

The claimed variety 'Looking Back' differs from its male parent 'Tying Shin Cupid' in that 'Looking Back' has flowers which are white with purple marks, whereas 'Tying Shin Cupid' has flowers which are purple and copper colored.

The claimed variety 'Looking Back' differs from its female parent 'Free Spirit' in that 'Looking Back' has flowers which are white with purple marks, whereas 'Free Spirit' has flowers which are white.

BRIEF DESCRIPTION OF THE PHOTOGRAPHS

The accompanying photographs illustrate the overall appearance of the new *Phalaenopsis* 'Looking Back' showing the colors as true as is reasonably possible with colored reproductions of this type. Colors in the photographs may differ slightly from the color values cited in the detailed botanical description, which accurately describe the color of 'Looking Back'.

DETAILED BOTANICAL DESCRIPTION

Figure 1:
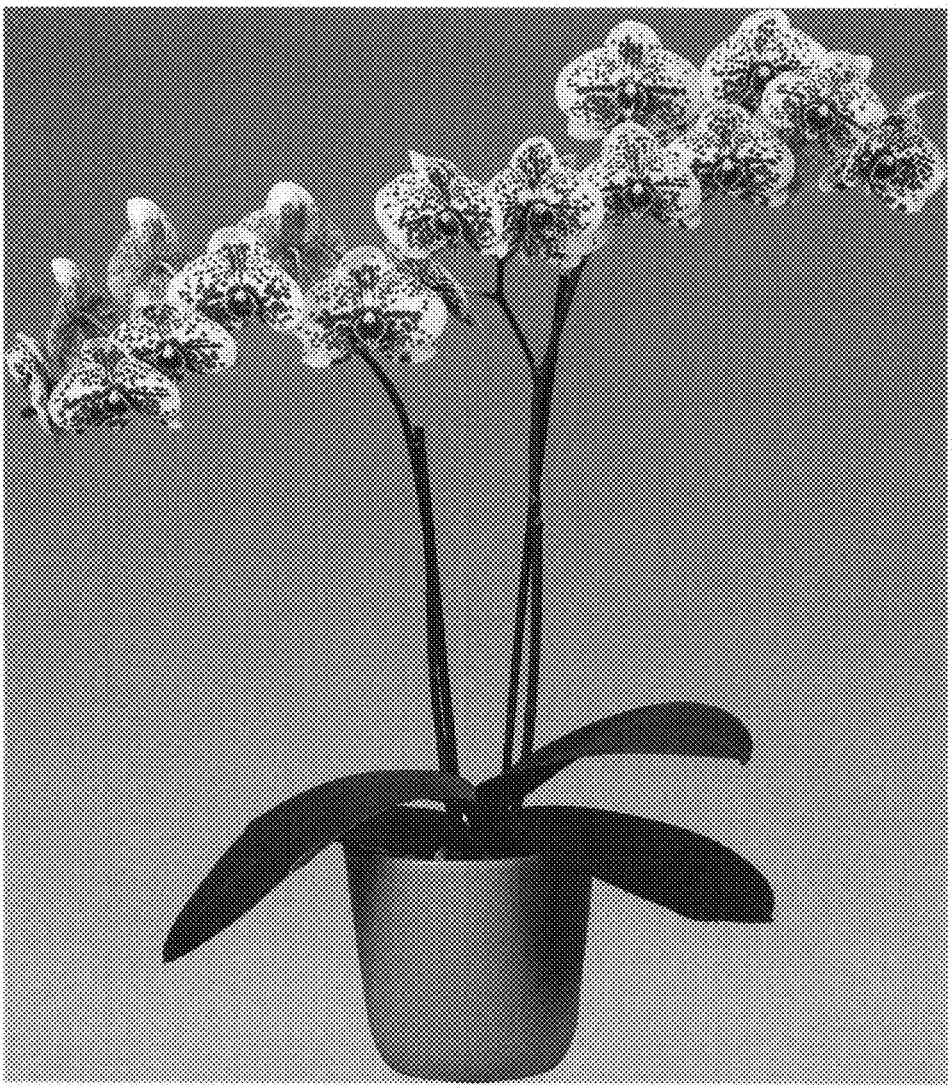
FIG. 1 shows a side view perspective of a typical flowering plant of 'Looking Back' in a 12 cm pot, at 16 months of age.

The new *Phalaenopsis* cultivar 'Looking Back' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Looking Back' as grown in a greenhouse in Strengweg, Heemskerk, The Netherlands, under conditions which closely approximate those generally used in commercial practice. Initially, the ideal temperature to grow plants of 'Looking Back' is 27° C. during the day and at night. Then, during the flowering phase of 'Looking Back', the ideal growing temperature is 20-22° C. during the day and 18° C. at night. Light levels for growing 'Looking Back' are a minimum of 5,000 lux and a maximum of 10,000 lux. A balanced fertilizer with level of 200 ppm N, 87 ppm P, 168 ppm K is applied. Duration of growth of 'Looking Back' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Looking Back' plants described is 12 months after potting.

Classification:

*Botanical.*—*Phalaenopsis hybrida.*

Parentage:

*Female or seed parent.*—*Phalaenopsis* cultivar designated 'Free Spirit', unpatented.

*Male or pollen parent.*—*Phalaenopsis* cultivar designated 'Tying Shin Cupid', unpatented.

Propagation:

*Type.*—Tissue culture.

*Rooting habit and description.*—Fleshy; approximately 5 mm-7 mm wide and green in color; freely branching. It takes 12 weeks for plants growing in tissue culture to initiate roots.

Plant:

*Size at maturity.*—Height: about 60 cm. Spread: about 70 to 80 cm.

*Growth habit.*—Standard; dark-green leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is blunt and asymmetric.

*Texture.*—Smooth and leathery.

*Pubescence.*—About 6 leaves.

*Mature leaf length.*—About 18 to 22 cm.

*Mature leaf width.*—About 8 to 10 cm.

*Mature leaf thickness.*—About 1.5 mm.

*Mature leaf color (both surfaces).*—RHS 137A.

*Venation.*—Pattern: parallel. Color of midvein: dark green RHS N137A.

Peduncle:

*Quantity per plant.*—About 1 to 2.

*Number of flowers per peduncle.*—About 10 to 18.

*Length.*—About 60 to 70 cm.

*Diameter.*—About 6 to 7 mm.

*Strength.*—Strong.

*Aspect.*—Upright.

*Texture.*—Glabrous and smooth.

*Color.*—Dark green (some RHS N189A and some RHS N137A, both colors individually present).

*Internode.*—Length: about 40 to 50 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 to 22 mm. Diameter (at midpoint): about 13 to 20 mm. Shape: egg-shaped. Color: young buds: RHS N144C with RHS N79A spots. Older buds: RHS 145B with RHS N79B spots.

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance*.—No fragrance.

Figure 2:
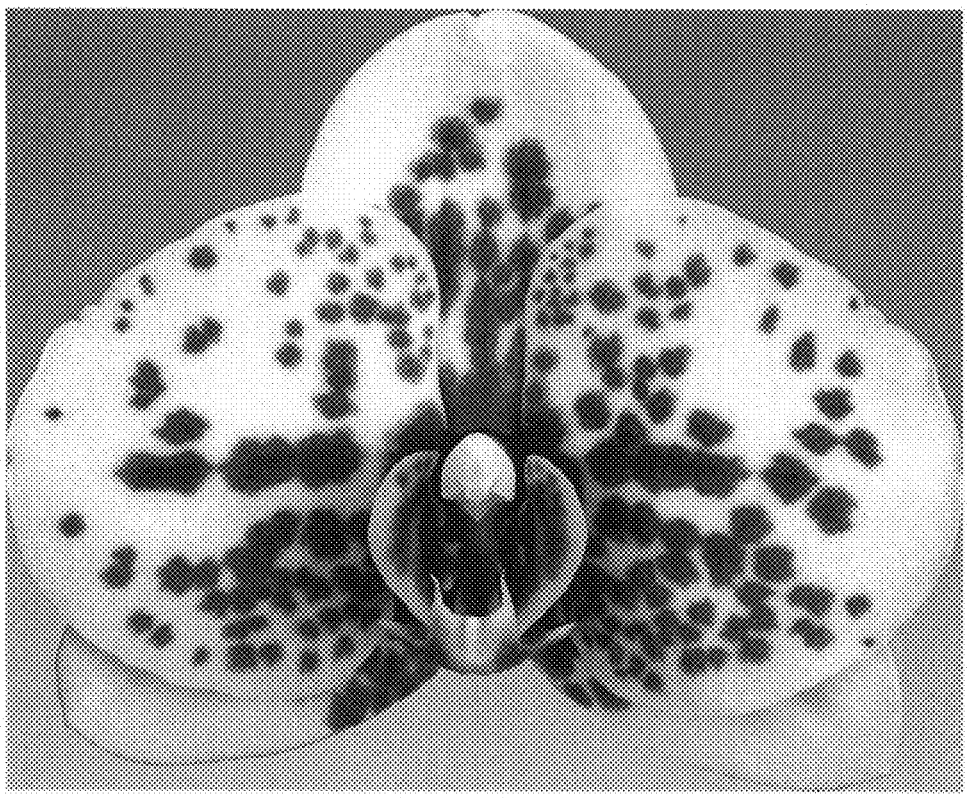
FIG. 2 shows a close-up view of the typical buds and flowers of 'Looking Back'.
Figure 3:
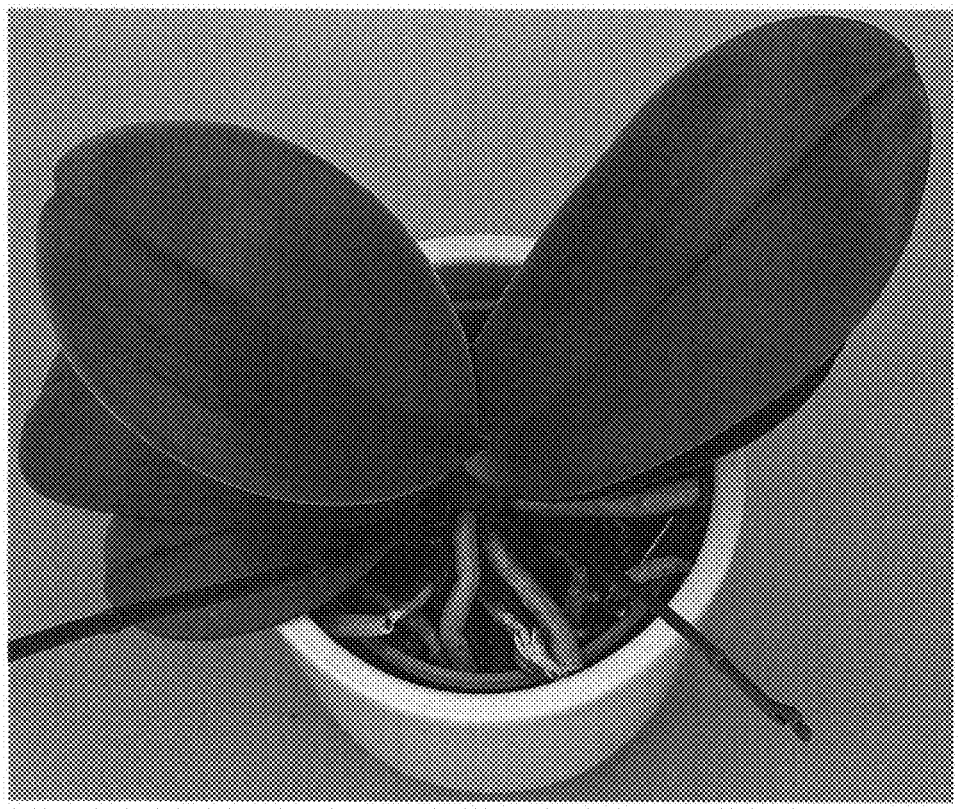
FIG. 3 shows a close-up view of the typical leaves of 'Looking Back'.

*Flower*.—Rate of opening: Flowers fully opened about 2 to 3 days after tepal separation. Orientation at opening: slanted upward and outward. Shape: see FIG. 2. Size: Height: about 75 mm. Diameter: about 90 mm. Depth of tube: about 8mm.

*Tepals*.—Quantity and arrangement: six tepals that are trimerous, overlapping and arranged in 2 whorls. Petals are more pronounced than sepals.

*Petals*.—Arrangement: Inner whorl of petals comprises 3 petals, 2 lateral petals and labellum. 2 lateral petals: Overall shape: broadly ovate and weakly cupped. Apex: oval. Margin: weakly undulate. Length: about 45 mm. Width: about 35 mm. Texture: Upper surface: smooth and satiny. Under surface: smooth and satiny. Color (when fully opened): upper side: main color is white (RHS NN155C) with purple spots (RHS N79C). Lower side: main color is white (RHS NN155C) with purple spots (some RHS N79C, some RHS N79D and some RHS N79B). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Length: about 23 mm. Width (not flattened): about 15 to 18 mm. Texture: Upper and lower surface: smooth and satiny. Color (when fully opened): Upper side: Main color is purple (RHS N79B). The edges of the lateral lobes and the mid lobe are yellow (RHS 13B). Lower side: main color is purple RHS N79B with yellow (RHS 13B). On the mid lobe some white (RHS NN155B). Chirri and column are white (RHS NN155B). The pestle is purple (RHS N92) with white (RHS NN155B) and some yellow (RHS 13B).

*Chirri*.—Short.

*Pestle* (*callosities*).—Length: about 4 mm. Width: about 5 mm.

*Sepals*.—Arrangement: Outer whorl of sepals comprises 3 sepals. Overall shape: Elliptical and weakly cupped. Length: about 30 mm to 40 mm. Width: about 30 mm to 35 mm. Texture: Upper and lower surface: smooth and satiny. Color (when fully opened): Upper side: white (RHS NN155C) with purple spots (RHS N79C). Lower side: white (RHS NN155C) with a purple haze (RHS 76A) and purple spots (RHS N79D, RHS N79B and some RHS N79C).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 8 mm. Diameter: about 6 mm. Color: white (RHS NN155B).

*Pollinia*.—Quantity: Two. Size: about 1 mm. Color: orange (RHS 25A).

*Ovary*.—Length: about 5 mm. Diameter: about 7 mm. Color: white RHS NN 155B.

*Pedicel*.—Length: about 35 mm to 55 mm. Diameter: about 4 mm. Color: close to the flower purple (RHS N79C), then white (RHS NN 155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Looking Back', as illustrated and described herein.

* * * * *